United States Patent [19]

Goupil

[11] Patent Number: 5,023,270

[45] Date of Patent: Jun. 11, 1991

[54] ANTIDEPRESSANT METHOD OF USE

[76] Inventor: Jean-Jacques Goupil, 30 Avenue du Président Wilson, 94230 Cachan, France

[21] Appl. No.: 337,814

[22] Filed: Apr. 13, 1989

[30] Foreign Application Priority Data

Apr. 14, 1988 [FR] France .................................. 88-04954

[51] Int. Cl.$^5$ .............................................. A61K 31/35
[52] U.S. Cl. ..................................................... 514/455
[58] Field of Search .......................................... 514/455

[56] References Cited

PUBLICATIONS

Chem. Abst. 109 (1988)–86241 H.

*Primary Examiner*—Stanley J. Friedman
*Attorney, Agent, or Firm*—Darby & Darby

[57] ABSTRACT

This invention concerns a pharmaceutical composition useful for treating depression in humans, comprising an effective amount of 5-methoxypsoralen, and optionally, a suitable carrier or diluent, e.g., carboxymethylcellulose, and optionally, a dispersing agent, e.g., polysorbate 80. Also disclosed is a method for treating depression, e.g., endogenous or clinical depression, comprising administering to humans in need of such treatment an effective amount of 5-methoxypsoralen, optionally, a pharmaceutically suitable carrier or diluent, and optionally, a dispersing agent.

11 Claims, 1 Drawing Sheet

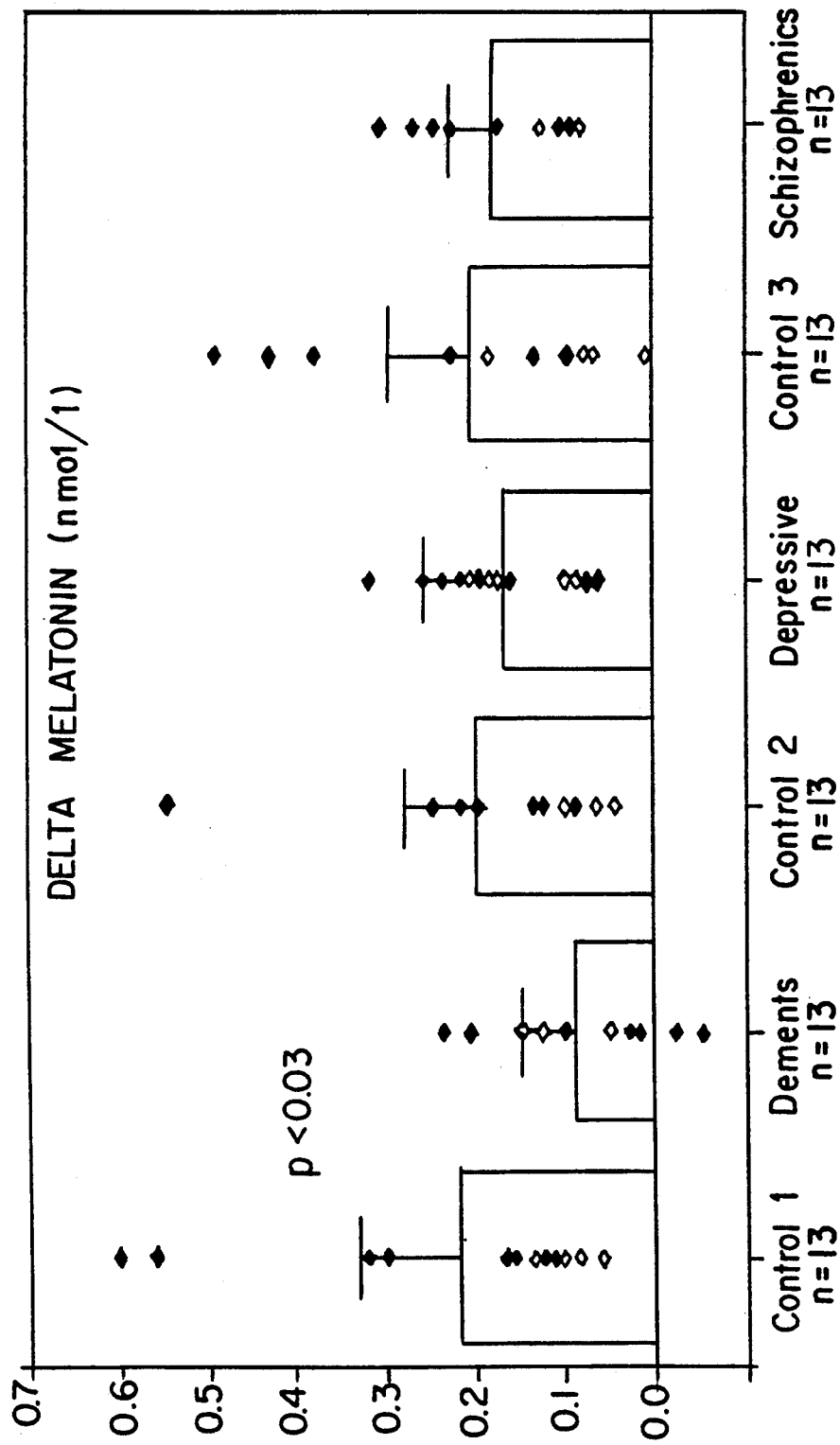

ANTIDEPRESSANT METHOD OF USE

FIELD OF THE INVENTION

The present invention concerns an antidepressant composition effective against endogenous depression, the compositions comprising 5-methoxypsoralen with the empirical formula $C_{12}H_8O_4$ as active ingredient.

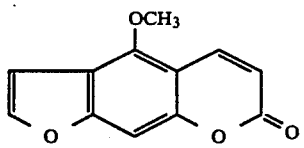

The invention also provides a method for treating humans having clinical depression.

BACKGROUND OF THE INVENTION

As a naturally occurring analog of psoralen and an isomer of methoxsalen 5-methoxypsoralen (hereinafter "5-MOP") is found in a variety of plants.

5-MOP has been employed in the treatment of psoriasis (See, e.g., the following: Belgium Patent No. 821,424 (Goupil), Feb. 2, 1979, which discloses pharmaceutical compositions for treating psoriasis containing 100 to 1000 ppm 5-MOP; U.S. Pat. Nos. 4,217,445 and 4,429,138 disclose processes for synthesizing 5-MOP; U.S. Pat. No. 4,699,781 discloses sun tanning products containing between about 2.75 to 27.5 mmg, i.e., mg 5-MOP per 100 gm of the product, an ultraviolet-B filtering agent and an oily excipient). It has also been proposed to use 5-MOP in the treatment of psoriasis when administered in combination with ultraviolet-A radiation (see H. Hoenigsmann, et al., *Brit. J. Dermatol.* 101: 369, 1979).

5-MOP has also been used to treat superficial skin cancers, such as dyskeratosis due to exposure to the sun, preinvasive epithelioma and basocellular epitheliomas (LaneBrown, M.L. and P. Forlot, "Photo-Onco Therapy (POT): An Alternative Modality for the Treatment of Superficial Skin Cancers", *Ann. Dermat. Venerol.*, 111(9):851, 1984; and *J. Invest. Dermat.*, 87:382, 1985. The acute effects which occur in humans with 5-MOP administration has also been investigated. Among such effects are increases in plasma melatonin levels at different times of the day, and retinal sensitivity to light.

SUMMARY OF THE INVENTION

The present invention concerns a pharmaceutical composition useful for treating depression in humans comprising an effective amount of 5-methoxypsoralen, and optionally, a suitable carrier or diluent, and optionally, a dispersing agent. This composition has been found to improve the depressive state of psychiatric patients, e.g., depressives, schizophrenics and dementia, as will be described below.

This invention also provides a method for treating depression in humans comprising administering to humans in need of such treatment an effective amount of 5-methoxypsoralen, and optionally, a suitable carrier or diluent, and optionally, a dispersing agent.

BRIEF DESCRIPTION OF THE FIGURE

FIG. 1 is a bar histogram which depicts the plasma melatonin levels in six diverse groups of human subjects before and after treatment with a single dose of 40 mg 5-methoxypsoralen (5-MOP) administered orally to each subject at 8:00 p.m. The subjects were maintained in total darkness or under weak illumination (without UV) for at least 9 hours after 5-MOP intake (corresponding to the sleep period). Blood samples were taken at 8:00 p.m. prior to 5-MOP administration and at 11:00 p.m. (see text for full description of experimental details). Plasma melatonin levels were evaluated by radioimmunology after extraction in diethylether using the method of Treifenaueret, Andres. Melatonin levels were established and compared with each group of subjects with similar age means using paired t-tests and between groups using unpaired t-tests. "$\Delta$-melatonin is defined as the difference between plasma melatonin levels (nmd/l) after 5-MOP uptake (3 hours after administration and $\Diamond$ =before 5-MOP administration; ◆=after 5-MOP uptake. (p=significance of difference between the two values.)

DETAILED DESCRIPTION OF THE INVENTION

All patents and literature references cited in this specification are hereby incorporated by reference in their entirety.

As used herein, the term "depression" refers to all forms of depression in humans including the psychiatric standards for depression defined in *Diagnostic and Statistical Manual(DSM III)*, American Psychological Association (APA). The use of "depression" herein is intended to embrace clinical and subclinical forms of depression, particularly endogenous depression whose onset is or does not appear to be brought on by any particular event in the subject human's life. Thus, the term "depression", as used herein includes depression clinically diagnosed by professionals, such as psychiatrists, psychotherapists, psychologists, and therapists, as well as depression which may not be clinically diagnosed by a mental health practitioner but may nevertheless still be severe and prolonged. By way of non-limiting examples, clinically diagnosed depression includes dementia, acute depression, schizophrenia, and other clinical depression disorders, classified, again, for example, in DSM III.

5-methoxypsoralen (5-MOP) is also known as bergaptene, bergapten, heraclin and majudin, and bears the chemical name 4-methoxy-7H-furo[3,2-g][1]benzopyran-7-one. 5-MOP is found in a variety of plants, e.g., oil or bergamot from *Citrus bergamio*, Aurantiodiae, *Fagara xanthoxyloides* and Rutaceae. The synthesis of 5-MOP is also well-described in the art (see, e.g, U.S. Pat. Nos. 4,217,445 and 4,429,138; see also Merck Index, Tenth Edition, No. 1166, p.1167, 1983 for other citations regarding the synthesis of 5-MOP).

The pharmaceutical compositions of this invention are useful for treating depression and oth.er similar abnormal mental states in humans. These compositions comprise an effective amount of 5-MOP, and optionally, a pharmaceutically acceptable carrier or diluent. The amount of 5-MOP in the composition is effective to increase plasma melatonin level in the human so treated for depression. As a further optional embodiment of this invention, the composition may comprise a suitable dispersing agent to aid in the solubilization of the active 5-MOP ingredient.

The effective amount of 5-MOP ranges from about 0.2 and 1 mg/kg body weight per day, preferably from about 0.4 to about 0.8 mg/kg body weight per day. The treatment duration may range from as little as one week but generally from about 2–3 weeks, up to 5 weeks or longer. Such amounts and duration may vary according to the individual subject (human), the severity of the depression and other factors which may affect the pharmaceutic kinetics of drug dosage and delivery. The influence of such factors on drug effectiveness is well-recognized in the art. It should be noted that the toxicity of 5-MOP is not a significant problem in mammals at the dosages contemplated herein, as will be exemplified in Example 1 to follow.

The suitable diluents or carriers in the compositions of this invention include a number of compounds known in the art and used for that purpose, for example, carboxymethylcellulose (CMC), starch, sterile water, and saline solution. Preferred in this invention is carboxymethylcellulose (CMC) in the form of a aqueous solution, e.g., 2% CMC.

The dispersing agents in the compositions herein include a number of suitable compounds, such as polysorbate 80 (sorbitan mono-9-octadecenoate poly (oxy-1,2-ethanediyl) derivatives, e.g., Tween ® 80 (Difco Laboratories, Detroit, Mich. 48232 and ICI America, Delaware). In particular, 5% Tween ® 80 may be employed according to this invention. The dispersing agent acts to solubilize or to disperse the "active" ingredient in the pharmaceutical composition or formulation. Preferred for use herein as a dispersing agent is Tween ® 80.

The compositions of this invention have been found to be useful in the treatment of depression in humans. For the purpose of the present invention, it is accepted in the art that depressions, e.g. endogenous depressions, are often accompanied by a certain number of circadian rhythm anomalies that resemble a perturbation in the drive of the biological clocks due to temporal landmarks in the environment. The existence of synchronization lapses is demonstrated by amplitude reduction and phase-instability of the biological rhythms (wakefulness/sleep, melatonin, cortisol, etc.).

While not wishing to be bound by any theory, it has been shown in the following examples that administration of 5-MOP at bedtime, according to the present invention, to diverse human psychiatric subjects, such as depressives, schizophrenics and dements, elicits a significant increase in the plasma melatonin level, thereby elevating the subject's mood and decreasing depression. With regard to depressive subjects, 5-MOP administration most preferably at bedtime, according to this invention, significantly improves the depressive state.

As used herein, the term "bedtime" refers to the nocturnal, i.e., normally the evening period for sleep which may vary, for example, in cases of severe depression, when the patient's sleep habits may not follow normal patterns. The term "bedtime" is intended to embrace the commonly accepted meaning of the term.

These compositions have been administered orally for ease of convenience, and allows the patient to follow the prescription although administration by a trained professional may be advisable.

The compositions of the present invention may be administered in a number of pharmaceutical formulations including, for example, tablets, caplets and gelluies which are preferably administered orally in, for example, 20 mg amounts of the active 5-MOP ingredient. Liquid formulations (oral or parenteral) are also contemplated. In addition, the compositions may take the form of so-called suppositories, suitable for rectal administration in, for example, 10 mg amounts of 5-MOP. Those skilled in the art will appreciate that the forms of the compositions and amounts of the 5-MOP therein, may vary within limits and still embrace the concept of this invention.

Furthermore, it has already been shown that administration of 5-MOP to perfectly sane human subjects results in increased melatonin secretion, while having no discernible effect on other endocrine hormones.

The present invention is further described in specific working examples which are intended to illustrate the present invention without limiting its scope.

EXAMPLE 1: TOXICITY OF 5-METHOXYPSORALEN (5-MOP)

Toxicity studies of 5-MOP in mice and male rats have shown that this molecule can be readily administered in large doses by virtue of its slight toxicity. These experiments are summarized below.

Animal trials were performed with mice and male rats free from specific pathogenic organisms, subject to a preliminary water diet for 18 hours. All animals were kept under observation during 14 days after a single oral administration, in order to detect any eventuality of toxic after effects. The median lethal dose LD50 and its confidence limits were computed by the graphic method of J. T. Litchfield and F. Wilcoxon.

Oral administration was used throughout the experiments, with an aqueous solution of 2% carboxymethylcellulose treated with Tween ®80 (Difco or ICI) at 5% as dispersing agent. Male mice showed a LD50 of 875 mg/kg in 14 days for 8-methoxypsoralen, and 8,100 mg/kg for 5-methoxypsoralen. The $LD_{50}$ in male rats was 4,400 mg/kg in 14 days for 8-methoxypsoralen, and more than 30,000 mg/kg for 5-methoxypsoralen.

The general, long-term toxicity of 5-MOP was also investigated in rabbits treated by ingestion and dermal application, with the following results:

For ingestive intake of 5-MOP during 42 consecutive days with a daily dosage of 300 mg/kg, toxicological tests (general condition, hematological and anatomico-pathological tests, skin and eye examinations, and clinical chemolysis) have demonstrated good tolerance to the novel composition. There was no suggestion in their observations that controlled clinical use in humans should be limited.

EXAMPLE 2: INVESTIGATION OF 5-METHOXYPSORALEN (5-MOP) ADMINISTRATION IN THE TREATMENT OF VARIOUS PSYCHIATRIC PATHOLOGIES

The experiment was performed on six groups of human subjects.

Control groups 1, 2 and 3 comprised respectively:

Group 1: 13 elderly, sane subjects (7 women, 6 men).

Group 2: 13 middle-aged, sane subjects (6 women, 7 men).

Group 3: 13 young, sane subjects (6 women, 7 men).

These subjects had been contacted for welfare or minor nervous problems, but were free from major psychiatric disorders or organic illnesses. Most aged subjects were waiting for admission to nursing homes.

Group 4 comprised 13 patients (7 women, 6 men) exhibiting all dementia criteria according to the DSM III classification. These elderly patients had no major cardiac, hepatic, renal, endocrineous or osseous disorders, nor any evolutionary pathology.

Group 5 comprised 13 subjects (8 women, 5 men) in an acute depressive phase, showing all symptoms of a major depressive disorder in the sense of DSM III.

Group 6 comprised 13 schizophrenic subjects (6 women, 7 men), according to DSM III criteria.

The diagnosis was established by means of a structured examination for affective disorders, schizophrenia and dementia, performed on each patient by two different psychiatrists. Any patient with a history of serious attendant illnesses, such as high blood pressure, diabetes, or other endocrineous pathologies, with distorted clinical or biological results, were excluded from the study. The patients received no medicaments 4 days prior to the experiment, except for 5 mg nitrazepam or 0.25 mg trazolam in the evening. All subjects participated voluntarily in the experiment and 5 were advised of its purpose. A single dose of 40 mg 5-methoxypsoralen (5-MOP) was given orally to all subjects at 8:00 p.m. To avoid any photosensitivity effects due to psoralen, patients were maintained in total darkness or under weak illumination (without UV) for at least 9 hours after 5-MOP intake (corresponding to the sleep period).

Blood samples were taken at 8:00 p.m., prior to 5-MOP administration, and again at 11:00 p.m., by means of a stationary catheter attached to the forearm at least twenty minutes before extraction of the first blood sample. Samples were immediately centrifuged at 4° C. and refrigerated at −20° C. until quantitative analysis. Plasma levels were evaluated by radioimmunology after extraction in diethylether, using the #method of Treifenaueret, Andres.

The reliability of melatonin quantitative analysis was verified by checking cross-reactions of other indolamines No correlation was observed between melatonin levels and absolute 5-MOP content at the dosage used.

Reactions within the same dosage were less than 6%, for a concentration of 0.58 nmol/1. Dosage accuracy was 0.0228 nmol/1.

Melatonin levels were established and compared within each group by means of paired t-tests, and between groups by unpaired t-tests.

Because age could influence endocrinous responses, only groups with similar age means were compared in these experiments.

"$\Delta$ melatonin" has been defined as the difference between melatonin levels after 5-MOP intake and the corresponding baseline values. The parameter "p" measures the significance of the difference between two values.

Experimental results are given below.

No patient exhibited side-effects after 5-MOP absorption. Results by groups are listed in Table 1 and FIG. 1.

FIG. 1 is a bar histogram depicting the results of Example 2. "◇" is the plasma melatonin level before 5-MOP administration; "◆" is the plasma melatonin level after 5-MOP uptake (3 hours after administration).

TABLE 1

Age and baseline plasma melatonin level means and SEM Post-5-MOP plasma melatonin levels and "$\Delta$ melatonin" are given for each group.

|  | n | Age | Melatonin (8:00 p.m.) | Melatonin (11:00 p.m.) | Delta Melatonin |
|---|---|---|---|---|---|
| CONTROL 1 | 13 | 73.31 ± 5.72 | 0.19 ± 0.05 | 0.42 ± 0.12 | 0.22 ± 0.11 |
| DEMENTS 1 | 13 | 77.92 ± 3.54 | 0.21 ± 0.06 | 0.30 ± 0.08 | 0.09 ± 0.06 |
| t and p Values |  | 1.56/0.133 | 0.55/0.589 | 1.88/0.073 | 2.4/0.025 |
| CONTROL 2 | 13 | 52.15 ± 7.55 | 0.16 ± 0.04 | 0.36 ± 0.09 | 0.20 ± 0.08 |
| DEPRESSIVES | 13 | 55.46 ± 9.49 | 0.22 ± 0.06 | 0.39 ± 0.15 | 0.17 ± 0.09 |
| t and p Values |  | 0.41/0.558 | 1.79/0.112 | 0.38/0.681 | 0.59/0.562 |
| CONTROL 3 | 13 | 33.46 ± 5.14 | 0.16 ± 0.05 | 0.36 ± 0.11 | 0.21 ± 0.09 |
| SCHIZOPHRENICS | 13 | 35.20 ± 6.54 | 0.21 ± 0.09 | 0.48 ± 0.09 | 0.15 ± 0.05 |
| t and p Values |  | 0.38/0.708 | 1.35/0.189 | 0.43/0.670 | 0.58/0.567 |

Melatonin levels are substantially higher in the control groups after 5-MOP intake ($t=4.59$, $p<0.01$; $t=4.18$, $p<0.001$; $t<3.92$, $p<0.001$). For dements $t=3.34$, $p<0.01$; for depressives $t=2.29$, $p<0.05$; for schizophrenics $t=8.31$, $p<0.0001$.

Mean "$\Delta$ melatonin" was substantially lower in the case of dements than for elderly control group subjects ($r=2.4$, $p<0.03$).

The same "$\Delta$ melatonin" was slightly lower in he gorup of depressives than in the control group, but not significantly so ($r=0.59$, $p<0.05$).

In conclusion, this experiment has shown a significant rise in plasma melatonin levels of psychiatric subjects after administration of 5-MOP. (See Table 1 and FIG. 1.)

EXAMPLE 3: CLINICAL STUDY OF THE ANTIDEPRESSANT EFFECT OF 5-METHOXYPSORALEN

Experimental verification of the clinical effects of 5-MOP on depressive patients was performed on 24 physically sane subjects (11 men and 13 women), suffering from a major depressive disorder.

Any subject exhibiting attendant psychiatric disorders, such as dementia, schizophrenia, or major somatic illnesses, was excluded from the investigation. Chosen patients afflicted with a major depressive disorder according to DSM III were given no treatment 4 days prior to the experiment, except for 5 mg nitrazepam in the evening.

The patients were divided into two groups. The first group was treated with a single daily dose of 40 mg 5-MOP during a week, administered orally at 9:00 p.m. The second group was given placebos, double blindly, under identical conditions.

To prevent any parallel effects due to the photosensitive properties of 5-MOP, patients were not exposed to ultraviolet (UV) radiation during nine hours following 5-MOP intake (corresponding to their sleep period).

After a week of treatment with 5-methoxypsoralen or placebos, clinical results were established for each patient group, and compared using the Wilcoxon test (W) within groups and the Mann-Whitney test (U) between groups. Results showed that no patient treated with 5-MOP suffered side effects. The baseline of quotations did not differ between groups. Patients having received placebos showed little or no improvement, while patients having received 5-MOP demonstrated significant improvement from their depressive state.

Clinical results using the 17 items are given in Table 2.

TABLE 2

| | | | Clinical results using the 17 HDRS items. | | | |
|---|---|---|---|---|---|---|
| | N | Sex Ratio | Average Age | HDRS J0 | HDRS J7 | W and p Values |
| MAJOR DEPRESSIVE DISORDER | | | | | | |
| PLACEBO | 12 | 6F/6M | 52.04 ± 12.11 | 22.33 ± 5.03 | 21.16 ± 5.02 | 15p 0.05 |
| 5-MOP | 12 | 7F/5M | 53.83 ± 13.16 | 21.92 ± 8.21 | 16.67 ± 7.99 | 3.5p 0.01 |
| U and P Values | | | 64/p 0.05 | 61/p 0.05 | 37/p 0.05 | |

From these data, it has been demonstrated that 5-MOP has particularly remarkable properties with regards to rapid improvement from depression, even at fairly small daily dosages.

In comparison to classical treatments of depressive states with tricyclics, the effectiveness of the composition provided by this invention, based on 5-methoxypsoralen, appears to be particularly high. In particular, the same results have been obtained, in terms of improvement in the patient's behavior, in one week of treatment with the novel composition instead of in a three week period of treatment with tricyclics.

The experiments have shown that administration of the composition must obligatorily take place in the evening at bedtime to insure the antidepressant effect described above.

Daily doses of 5-methoxypsoralen administered orally vary between 0.2 and 1 mg/kg body weight, usually between 0.4 and 0.8 mg/kg body weight. Treatment duration is of the order of between 2 to 3 weeks and 5 weeks.

Maintenance treatments to prevent relapses may include administration of the useful dose once or twice weekly during a period of about one or two weeks.

It is noteworthy that the full effect of the novel composition and method that is the subject of this invention is obtained without irradiation of-patients by ultraviolet-A (UVA) radiation.

What is claimed is:

1. A method of treating depression in a human in need of such treatment comprising administering at bedtime to a human in need of such treatment, a composition comprising an effective amount of 5-methoxypsoralen.

2. The method of claim 1, said composition further comprising a pharmaceutically suitable carrier or diluent.

3. The method of claim 2, said composition further comprising a dispersing agent.

4. A method according to claim 1, which comprises administering said 5-methoxypsoralen to a human having depression selected from the group consisting of endogenous depression, acute depression, chronic depression, schizophrenia, and dementia, and combinations of two or more of the foregoing illnesses.

5. A method according to claim 1, which comprises administering an effective amount of 5-methoxypsoralen comprising from about 0.02 to about 1 mg/kg body weight per day.

6. A method according to claim 5, wherein the effective amount comprises from about 0.04 to about 0.8 mg/kg body weight per day.

7. A method according to calim 2, which comprises administering a pharmaceutically suitable carrier or diluent selected from the group consisting of carboxymethylcellulose, starch, sterile water, and saline solution, and combinations of two or more of the foregoing.

8. A method according to claim 3, which comprises administering a dispersing agent comprising polysorbate 80.

9. A method according to claim 1, which comprises administering said composition orally.

10. A method according to claim 1, wherein said administration is rectal administration.

11. A method according to claim 1, which comprises administering said composition daily for a period of from about 1 to about 5 weeks.

* * * * *